United States Patent
Gatti McArthur et al.

(10) Patent No.: US 7,511,033 B2
(45) Date of Patent: Mar. 31, 2009

(54) DIHYDRO-BENZO[B][1,4]DIAZEPIN-2-ONE SULFONAMIDE DERIVATIVES

(75) Inventors: Silvia Gatti McArthur, Basel (CH); Juergen Wichmann, Steinen (DE); Thomas Johannes Woltering, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/102,140

(22) Filed: Apr. 14, 2008

(65) Prior Publication Data

US 2008/0261957 A1    Oct. 23, 2008

(30) Foreign Application Priority Data

Apr. 19, 2007   (EP) ................. 07106522

(51) Int. Cl.
  C07D 243/24    (2006.01)
  A61K 31/5513   (2006.01)
  A61P 25/00     (2006.01)
(52) U.S. Cl. ....................... 514/221; 540/517
(58) Field of Classification Search ............. 540/517; 514/221
See application file for complete search history.

(56) References Cited

U.S. PATENT DOCUMENTS

| | | | |
|---|---|---|---|
| 5,716,953 | A | 2/1998 | Donati et al. |
| 6,051,712 | A | 4/2000 | Binggeli et al. |
| 6,407,094 | B1 | 6/2002 | Adam et al. |
| 6,544,985 | B2 | 4/2003 | Adam et al. |
| 6,548,495 | B2 | 4/2003 | Adam et al. |
| 6,949,542 | B2 | 9/2005 | Adam et al. |

FOREIGN PATENT DOCUMENTS

| | | |
|---|---|---|
| EP | 0487155 | 5/1992 |
| JP | SHO 60-32775 | 2/1985 |
| JP | SHO-62174062 | 7/1987 |
| JP | HEI 4-283572 | 10/1992 |
| WO | WO 92/03438 | 3/1992 |
| WO | WO 94/03437 | 2/1994 |
| WO | WO 96/05818 | 2/1996 |
| WO | WO 97/05109 | 2/1997 |
| WO | WO 99/26927 | 6/1999 |
| WO | WO 01/10846 | 2/2001 |
| WO | WO 01/29011 | 4/2001 |
| WO | WO 01/29012 | 4/2001 |
| WO | WO 02/083652 | 10/2002 |
| WO | WO 02/083665 | 10/2002 |
| WO | WO 03/066623 | 8/2003 |

OTHER PUBLICATIONS

Cartmell, et al. Br. J. Pharmacol. 1998, vol. 123(3) pp. 497-504.
Wilson, J., et al., J. Chem. 1983, vol. 36, pp. 2317-2325.
Giroux et al., Tetr. Lett. 1997, vol. 38, pp. 3841-3844.
Ishiyama et al., Tetr. Lett. 1993, vol. 34, pp. 7595-7598.
Kosugi et al., Bull. Chem. Soc. Jpn. 1983, vol. 56, pp. 3855-3856.
Thorand et al., J. Org. Chem. 1998, vol. 63, pp. 8551-8553.
Bellamy et al., Tetr. Lett. 1984, vol. 25 pp. 839-842.
Rathke et al. Synth. Commun. 1985, vol. 15 pp. 1039-1049.
Hagedorn et al., J. Med. Chem. 1987, vol. 30, pp. 1342-1347.
Larsen, et al., Tetrahedron, 1984, vol. 40, pp. 2985-2988.
Hiromichi et al., Chem. Pharm. Bull. 1983, vol. 31, pp. 1896-1901.
Winkler et al., Tetrahedron Lett., 1998, vol. 39, pp. 2253-2256.
Masayoshi e tal., Journal of Antibiotics, 1978, vol. 31, pp. 1245-1251.
Beny et al., J. Org. Chem. 1982, vol. 47, pp. 2201-2204.
Corey et al., J. Org. Chem. vol. 38, No. 18, p. 3224, 1973.
Brauner-Osborne et al., Ligands for Glutamate Receptor: Design and Therapeutic Prospects, J. Med. Chem. vol. 43, pp. 2609-2645 (2000).
CAS Printout for JP62174062, Chem. Abstracts vol. 108:75434 (1987).
CAS Printout for Solomko et al., Chem. Abstracts vol. 102:132005.
CAS Printout for Solomko et al., Chem. Abstracts vol. 102:6436.
CAS Printout for Bougrin et al., Chem. Abstracts vol. 122:239666.
CAS Printout for Hamdi et al., Chem. Abstracts vol. 121:83303.
CAS Printout for Rao et al., Chem. Abstracts vol. 117:69839.
Hanumantha, Rao, et al., Synthesis vol. 5, pp. 446-448 (1992).
Achmatowicz et al., Tetrahedron Lett. vol. 27 pp. 1973-1996 (1971).
Boyer et al., J. Heterocyclic Chem. vol. 25, pp. 1003-1005 (1988).
Ohmori et al., J. Med. Chem. vol. 37 pp. 467-475 (1994).
Ishikawa et al., J. Med. Chem. vol. 28 pp. 1387-1393 (1985).
Fanta et al., Organic Syntheses vol. 25 pp. 78-80 (1945).
Eicher et al., Synthesis pp. 755-762 (1996).
Widmer, Synthesis pp. 135-136 (1983).
Bowman et al., Org. Prep. Proc. Int. vol. 22 No. 5 pp. 636-638 (1990).
Quallich et al., Synthesis pp. 51-53 (1993).
Cheng et al., Biochem. Pharmacol. vol. 22 pp. 3099-3108 (1973).
Chemical Abstracts 87:167993 (1977).
Bougrin et al., Tetrahedron Letters (1994) vol. 35 pp. 8373-8376.
D'Onofrio et al., J. Neurochem. (2003) vol. 84(6) pp. 1288-1295.

*Primary Examiner*—Bruck Kifle
(74) *Attorney, Agent, or Firm*—George W. Johnston; Patricia S. Rocha-Tramaloni; Kimberly J. Prior

(57) ABSTRACT

The present invention relates to compounds of formula (I), a process for the manufacture thereof, their use for the preparation of medicaments for treating CNS disorders and pharmaceutical compositions containing them. Compounds of formula (I) are represented by general formula (I)

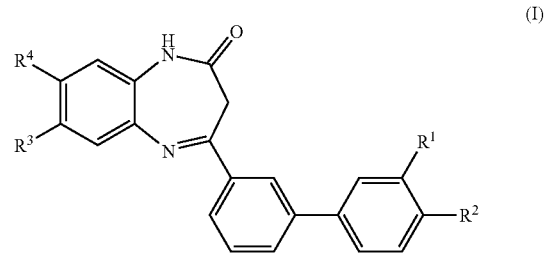

wherein $R^1$, $R^2$, $R^3$ and $R^4$ are defined as in the specification.

13 Claims, No Drawings

DIHYDRO-BENZO[B][1,4]DIAZEPIN-2-ONE SULFONAMIDE DERIVATIVES

PRIORITY TO RELATED APPLICATION(S)

This application claims the benefit of European Patent Application No. 07106522.1, filed Apr. 19, 2007, which is hereby incorporated by reference in its entirety.

BACKGROUND OF THE INVENTION

In the central nervous system (CNS) the transmission of stimuli takes place by the interaction of a neurotransmitter, which is sent out by a neuron, with a neuroreceptor.

L-glutamic acid, the most commonly occurring neurotransmitter in the CNS, plays a critical role in a large number of physiological processes. The glutamate-dependent stimulus receptors are divided into two main groups. The first main group forms ligand-controlled ion channels. The metabotropic glutamate receptors (mGluR) form the second main group and, furthermore, belong to the family of G-protein-coupled receptors.

At present, eight different members of these mGluR are known and of these some even have sub-types. On the basis of structural parameters, the different influences on the synthesis of secondary metabolites and the different affinity to low-molecular weight chemical compounds, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the group II can be used for the treatment or prevention of acute and/or chronic neurological disorders such as psychosis, schizophrenia, Alzheimer's disease, cognitive disorders and memory deficits.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are chronic and acute pain, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia, depressions, colon cancer, sleep disorders, disorders of circadian rhythms and glioma since mGluR2 antagonists have been found to reduce cell proliferation in human glioma cells (J. Neurochem. March 2003, 84(6): 1288-95).

SUMMARY OF THE INVENTION

The present invention provides compounds of formula I, a process for the manufacture thereof, their use for the preparation of medicaments for treating CNS disorders and pharmaceutical compositions containing them. In particular, the invention provides compounds of formula I

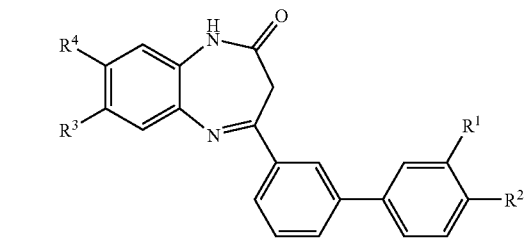

(I)

wherein:
$R^1$ is H and $R^2$ is $-S(O)_2-NR^aR^b$ or $R^2$ is H and $R^1$ is $-S(O)_2-NR^aR^b$;
$R^3$ is H, fluoro, chloro, $C_{1-6}$-alkyl, $C_{1-6}$-haloalkyl, $C_{1-6}$-alkoxy, $C_{1-6}$-haloalkoxy or $NR^aR^b$;
$R^4$ is chloro, $C_{1-6}$-haloalkyl or aryl optionally substituted by halogen; and
$R^a$ and $R^b$ are independently selected from the group consisting of H, $C_{1-6}$-alkyl and $C_{2-6}$-hydroxyalkyl;

as well as pharmaceutically acceptable salts thereof.

Compounds of general formula I are metabotropic glutamate receptor antagonists. Compounds of formula I are distinguished by valuable therapeutic properties.

The compounds of formula (I) can also be used in form of their prodrugs. Examples are esters, N-oxides, phosphate esters, glycoamide esters, glyceride conjugates and the like. The prodrugs may add to the value of the present compounds advantages in absorption, pharmacokinetics in distribution and transport to the brain.

DETAILED DESCRIPTION OF THE INVENTION

Unless otherwise stated, the following terms used in the present description have the definitions given in the following.

The term "alkyl" or "$C_{1-6}$-alkyl" denotes straight-chain or branched saturated hydrocarbon residues with 1 to 6 carbon atoms ($C_{1-6}$-alkyl), preferably with 1 to 4 carbon atoms, such as methyl, ethyl, n-propyl, i-propyl, i-butyl, t-butyl, as well as those groups which are illustrated with the exemplified compounds of the invention hereinafter.

The term "$C_{1-6}$-haloalkyl" denotes a $C_{1-6}$-alkyl group as defined hereinabove, which is substituted by one or more halogen atom(s), in particular Cl, F or I, preferably three Cl or two or three F, i.e. $CCl_3$, $CHF_2$ and $CF_3$ as well as those groups which are specifically illustrated with the exemplified compounds of the invention hereinafter.

The term "$C_{1-6}$-hydroxyalkyl" denotes a $C_{1-6}$-alkyl group as defined hereinabove, which is substituted by one or more, preferably, one, two or three, and still more preferably one, hydroxy group(s) (OH).

The term "$C_{1-6}$-alkoxy" denotes a $C_{1-6}$-alkyl residue as defined above bound via an oxygen atom. Examples of "$C_{1-6}$-alkoxy" residues include methoxy, ethoxy, isopropoxy, as well as those groups which are illustrated with the exemplified compounds of the invention hereinafter.

The term "$C_{1-6}$-haloalkoxy" denotes a $C_{1-6}$-alkoxy group as defined hereinabove, which is substituted by one or more halogen atom(s), in particular Cl, F or I, preferably three Cl or two or three F, i.e. $OCHF_2$ and $OCF_3$, $OCH_2CHF_2$, $OCH_2CF_3$ as well as those groups which are specifically illustrated with the exemplified compounds of the invention hereinafter.

The term "aryl" denotes a monovalent cyclic aromatic hydrocarbon radical, for example phenyl, naphthyl, biphenyl or indanyl.

The expression "R together with boron and both oxygens form a 5- or 6-membered heterocycloalkyl ring" denotes an unsubstituted or substituted heterocyclic ring having 5 or 6 ring members comprising at least one boron atom and two oxygen atoms connected thereto, the remaining ring members being carbon atoms. Examples of such heterocycloalkyl groups are 4,4,5,5-tetramethyl-[1,3,2]dioxaborolanyl or 5,5-dimethyl-[1,3,2]dioxaborinanyl. Substituents are preferably one to four $C_{1-6}$-alkyl such as e.g. methyl.

The term "halogen" embraces fluorine (F), chlorine (Cl), bromine (Br) and iodine (I).

The term "optionally substituted" means that the chemical group to which it refers can be substituted by one or more of the substituents recited in this connection, for example by one, two, three, four, five, six, seven, eight, nine or ten, preferably one to three substituents, depending on the valence and available positions of said chemical group.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable addition salt" refers to any salt derived from an inorganic or organic acid or base.

"Therapeutically effective amount" means an amount that is effective to prevent, alleviate or ameliorate symptoms of disease or prolong the survival of the subject being treated.

The compounds of formula (I) and their pharmaceutically acceptable salts are metabotropic glutamate receptor antagonists and can be used for the treatment or prevention of acute and/or chronic neurological disorders, such as psychosis, schizophrenia, Alzheimer's disease, cognitive disorders and memory deficits. Other treatable indications are restricted brain function caused by bypass operations or transplants, poor blood supply to the brain, spinal cord injuries, head injuries, hypoxia caused by pregnancy, cardiac arrest and hypoglycaemia. Further treatable indications are acute and chronic pain, Huntington's chorea, ALS, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia, depression, colon cancer, sleep disorders, disorders of circadian rhythms and glioma.

Also encompassed by the compounds of formula (I) according to the invention are the compounds wherein:
$R^1$ is H and $R^2$ is —$S(O)_2$—$NR^aR^b$ or $R^2$ is H and $R^1$ is —$S(O)_2$—$NR^aR^b$;
$R^3$ is H, $C_{1-6}$-alkyl, $C_{1-6}$-alkoxy, or $NR^aR^b$;
$R^4$ is $C_{1-6}$-haloalkyl or aryl optionally substituted by halogen; and $R^a$ and $R^b$ are independently selected from the group consisting of H and $C_{1-6}$-alkyl;

as well as pharmaceutically acceptable salts thereof.

In a certain embodiment, the compound of formula (I) according to the invention are those wherein $R^1$ is H and $R^2$ is —$S(O)_2$—$NR^aR^b$.

When $R^1$ is H and $R^2$ is —$S(O)_2$—$NR^aR^b$, $R^a$ and $R^b$ can be both H, comprising for example the following compounds:
3'-(8-Methyl-4-oxo-7-trifluoromethyl-4,5-dihydro-3H-benzo[b][1,4]diazepin-2-yl)-biphenyl-4-sulfonic acid amide;
3'-(4-Oxo-7-trifluoromethyl-4,5-dihydro-3H-benzo[b][1,4]diazepin-2-yl)-biphenyl-4-sulfonic acid amide;
3'-(8-Ethoxy-4-oxo-7-trifluoromethyl-4,5-dihydro-3H-benzo[b][1,4]diazepin-2-yl)-biphenyl-4-sulfonic acid amide;
3'-(8-Dimethylamino-4-oxo-7-trifluoromethyl-4,5-dihydro-3H-benzo[b][1,4]diazepin-2-yl)-biphenyl-4-sulfonic acid amide;
3'-[8-(Isobutyl-methyl-amino)-4-oxo-7-trifluoromethyl-4,5-dihydro-3H-benzo[b][1,4]diazepin-2-yl]-biphenyl-4-sulfonic acid amide;
3'-[7-(2-Fluoro-phenyl)-4-oxo-4,5-dihydro-3H-benzo[b][1,4]diazepin-2-yl]-biphenyl-3-sulfonic acid amide; and
3'-(8-Isobutylamino-4-oxo-7-trifluoromethyl-4,5-dihydro-3H-benzo[b][1,4]diazepin-2-yl)-biphenyl-4-sulfonic acid amide.

When $R^1$ is H and $R^2$ is —$S(O)_2$—$NR^aR^b$, $R^a$ can be H and $R^b$ can be $C_{1-6}$-alkyl, comprising for example the following compounds:
3'-(4-Oxo-7-trifluoromethyl-4,5-dihydro-3H-benzo[b][1,4]diazepin-2-yl)-biphenyl-4-sulfonic acid tert-butylamide; and
3'-(8-Ethoxy-4-oxo-7-trifluoromethyl-4,5-dihydro-3H-benzo[b][1,4]diazepin-2-yl)-biphenyl-4-sulfonic acid tert-butylamide.

In another embodiment, the compound of formula (I) according to the invention are those wherein $R^2$ is H and $R^1$ is —$S(O)_2$—$NR^aR^b$.

When $R^2$ is H and $R^1$ is —$S(O)_2$—$NR^aR^b$, $R^a$ and $R^b$ can be both H, comprising for example the following compounds:
3'-(8-Methyl-4-oxo-7-trifluoromethyl-4,5-dihydro-3H-benzo[b][1,4]diazepin-2-yl)-biphenyl-3-sulfonic acid amide;
3'-(4-Oxo-7-trifluoromethyl-4,5-dihydro-3H-benzo[b][1,4]diazepin-2-yl)-biphenyl-3-sulfonic acid amide;
3'-(8-Ethoxy-4-oxo-7-trifluoromethyl-4,5-dihydro-3H-benzo[b][1,4]diazepin-2-yl)-biphenyl-3-sulfonic acid amide;
3'-(8-Dimethylamino-4-oxo-7-trifluoromethyl-4,5-dihydro-3H-benzo[b][1,4]diazepin-2-yl)-biphenyl-3-sulfonic acid amide;
3'-[8-(Isobutyl-methyl-amino)-4-oxo-7-trifluoromethyl-4,5-dihydro-3H-benzo[b][1,4]diazepin-2-yl]-biphenyl-3-sulfonic acid amide;
3'-[7-(2-Fluoro-phenyl)-4-oxo-4,5-dihydro-3H-benzo[b][1,4]diazepin-2-yl]-biphenyl-4-sulfonic acid amide; and
3'-(8-Isobutylamino-4-oxo-7-trifluoromethyl-4,5-dihydro-3H-benzo[b][1,4]diazepin-2-yl)-biphenyl-3-sulfonic acid amide.

When $R^2$ is H and $R^1$ is —$S(O)_2$—$NR^aR^b$, $R^a$ can be H and $R^b$ can be $C_{1-6}$-alkyl, comprising for example the following compounds:
3'-(8-Methyl-4-oxo-7-trifluoromethyl-4,5-dihydro-3H-benzo[b][1,4]diazepin-2-yl)-biphenyl-3-sulfonic acid tert-butylamide;
3'-(4-Oxo-7-trifluoromethyl-4,5-dihydro-3H-benzo[b][1,4]diazepin-2-yl)-biphenyl-3-sulfonic acid tert-butylamide; and
3'-(8-Ethoxy-4-oxo-7-trifluoromethyl-4,5-dihydro-3H-benzo[b][1,4]diazepin-2-yl)-biphenyl-3-sulfonic acid tert-butylamide.

In a further embodiment, the invention relates to a pharmaceutical composition containing a compound of formula I according to the invention for the prevention or the treatment of a disease or condition in which mGluR2 activation plays a role or is implicated, for example the prevention or the treatment of acute and/or chronic neurological disorders such as psychosis, schizophrenia, Alzheimer's disease, cognitive disorders, memory deficits, colon cancer, sleep disorders, disorders of circadian rhythms and glioma.

Still in a further embodiment, the invention provides a method for the treatment of a disease or condition in which mGluR2 activation plays a role or is implicated, for example the treatment and/or prevention of acute and/or chronic neurological disorders comprising psychosis, schizophrenia, Alzheimer's disease, cognitive disorders, memory deficits, colon cancer, sleep disorders, disorders of circadian rhythms and glioma. These methods comprise administering to an individual, a therapeutically effective amount of a compound of formula (I) or a pharmaceutically acceptable salt thereof.

The compounds of the invention can be prepared by process comprising the step of reacting a compound of formula V with a compound of formula VI:

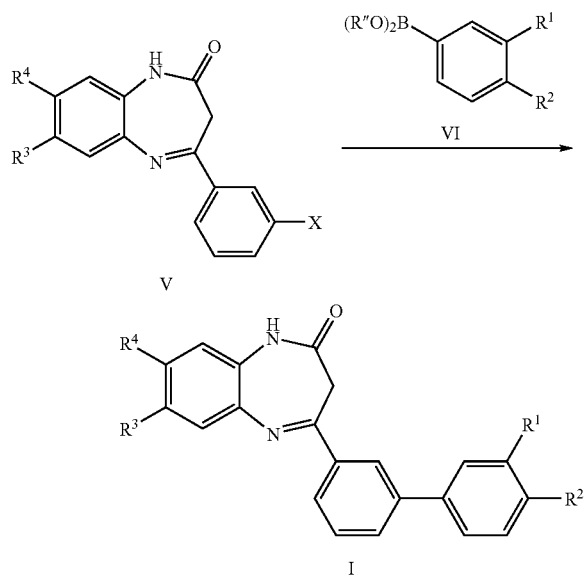

wherein X is chlorine, bromine, iodine, R" is H, $C_{1-6}$-alkyl or together with boron and both oxygens form a 5- or 6-membered heterocycloalkyl ring like e.g. in 4,4,5,5-tetramethyl-[1,3,2]dioxaborolanyl or 5,5-dimethyl-[1,3,2]dioxaborinanyl, $R^b$ is either H or $C_{1-6}$-alkyl and $R^3$ and $R^4$ are as defined hereinabove.

In a certain embodiment of the process according to the invention, the step of reacting a compound of formula V with a compound of formula VI comprises using a palladium catalyst such as e.g. tetrakis(triphenylphosphine)palladium.

In any one of the embodiments of the process according to the invention, the step of reacting a compound of formula V with a compound of formula VI comprises using an organic solvent (e.g. 1,2-dimethoxy-ethane).

In any one of the embodiments of the process according to the invention X is preferably either Br or I.

In any one of the embodiments of the process according to the invention R" is preferably H, $C_{1-6}$-alkyl or together with the boron atom and both oxygens form a 5- or 6-membered heterocyclic ring like e.g. in 4,4,5,5-tetramethyl-[1,3,2]dioxaborolanyl or 5,5-dimethyl-[1,3,2]dioxaborinanyl.

The invention also extends to the product obtained by the above described process.

The starting products, intermediates products and reagents for this process are either commercially available or can be prepared as described in the examples hereinafter.

All detailed procedures for the respective compounds can be found in the description of the examples.

The compounds of the present invention are group II mGlu receptor antagonists. The compounds show activities, as measured in the assay described below, of 0.250 μM or less, typically 0.100 μM or less, and ideally of 0.010 μM or less. In the table below are described some specific Ki values of some preferred compounds.

| | Ex. No. | | | | | | |
|---|---|---|---|---|---|---|---|
| | 1 | 2 | 3 | 4 | 5 | 6 | 7 |
| $K_i$ mGlu2 (μM) | 0.0019 | 0.02 | 0.0009 | 0.012 | 0.016 | 0.009 | 0.03 |

| | Ex. No. | | | | | | |
|---|---|---|---|---|---|---|---|
| | 8 | 9 | 10 | 11 | 12 | 13 | 14 |
| $K_i$ mGlu2 (μM) | 0.0017 | 0.003 | 0.0027 | 0.003 | 0.0031 | 0.0012 | 0.017 |

| | Ex. No. | | | | |
|---|---|---|---|---|---|
| | 15 | 16 | 17 | 18 | 19 |
| $K_i$ mGlu2 (μM) | 0.0087 | 0.0056 | 0.0022 | 0.021 | 0.0036 |

[$^3$H]-LY354740 Binding on mGlu2 Transfected CHO Cell Membranes.

Transfection and Cell Culture cDNA encoding the rat mGlu2 receptor protein in pBluescript II was subcloned into the eukaryotic expression vector pcDNA I-amp from Invitrogen Ltd (Paisley, UK). This vector construct (pcD1 mGR2) was co-transfected with a psvNeo plasmid encoding the gene for neomycin resistance, into CHO cells by a modified calcium phosphate method described by Chen & Okayama (1988). The cells were maintained in Dulbecco's Modified Eagle medium with reduced L-glutamine (1 mM final concentration), 36 mg/L L-Proline and 10% dialysed foetal calf serum from Gibco-Invitrogen; the medium was supplemented with 500 microM α-methyl-4-carboxyphenylglycine (MCPG). Selection was made in the presence of G-418 (300 ug/ml final concentration). Clones were identified by reverse transcription of 5 μg total RNA, followed by PCR using mGlu2 receptor specific primers 5'-atcactgcttgggtttctggcactg-3' and 5'-agcatcactgtgggtggcat-aggagc-3' in 60 mM Tris HCl (pH 10), 15 mM $(NH4)_2SO_4$, 2 mM $MgCl_2$, 25 units/ml Taq Polymerase with 30 cycles annealing at 60° C. for 1 min., extension at 72° C. for 30 s, and 1 min. 95° C. denaturation.

Membrane Preparation

Cells, cultured as above, were harvested and washed three times with cold PBS and frozen at −80° C. The pellet was resuspended in cold 20 mM HEPES-NaOH buffer containing 10 mM EDTA (pH 7.4), and homogenized with a polytron (Kinematica, AG, Littau, Switzerland) for 10 s at 10 000 rpm. After centrifugation for 30 min. at 4° C., the pellet was washed once with cold 20 mM HEPES-NaOH buffer containing 0.1 mM EDTA, (pH 7.4). After a second centrifugation for 30 min. at 4° C. the pellet was resuspended in cold 20 mM HEPES-NaOH buffer containing 0.1 mM EDTA, (pH 7.4). Protein content was measured using the Micro BCA method from Pierce-Perbio (Rockford, Ill., USA) using bovine serum albumin as standard.

[³H]-LY354740 Binding

After thawing, the membranes were resuspended in cold 50 mM Tris-HCl buffer containing 2 mM $MgCl_2$ (pH 7.4) (binding buffer). The final concentration of the membranes in the assays was 25 μg protein/ml. Inhibition experiments were performed with membranes incubated with 10 nM [³H]-LY354740 at room temperature, for 1 hour, in presence of various concentrations of the compound to be tested. Following the incubations, membranes were filtered onto Whatmann GF/B glass fiber filters or onto GF/B Unifilter plates and washed 5 times with cold binding buffer. Non specific binding was measured in the presence of 10 μM (2S,2'R,3'R)-2-(2'3'-Dicarboxycyclopropyl)glycine (DCG IV from Tocris, Ellisville, Mo. USA). After transfer of the filters into plastic vials containing 10 ml of Ultima-gold scintillation fluid from Perkin-Elmer (Boston, Mass., USA), the radioactivity was measured by liquid scintillation in a Tri-Carb 2500 TR counter (Packard, Zürich, Switzerland). For 96-Unifilter plates the radioactivity was measured after addition of Microscint 40 scintillation fluid (Perkin Elmer, Boston Mass.) using a Top-Count NXT (Packard)

Data Analysis.

The inhibition curves were fitted with a four parameter logistic equation giving $IC_{50}$ values, and Hill coefficients.

EXAMPLES

Scheme A

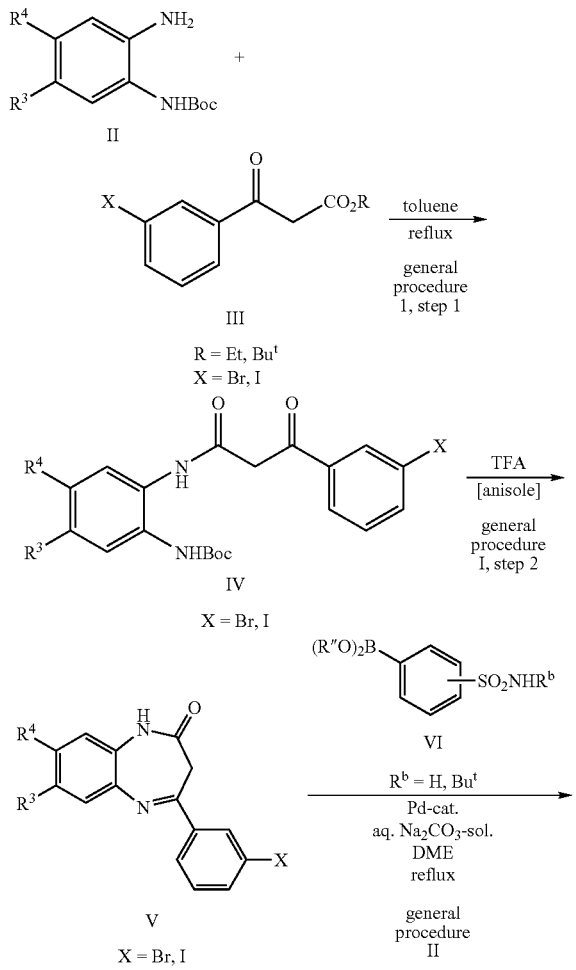

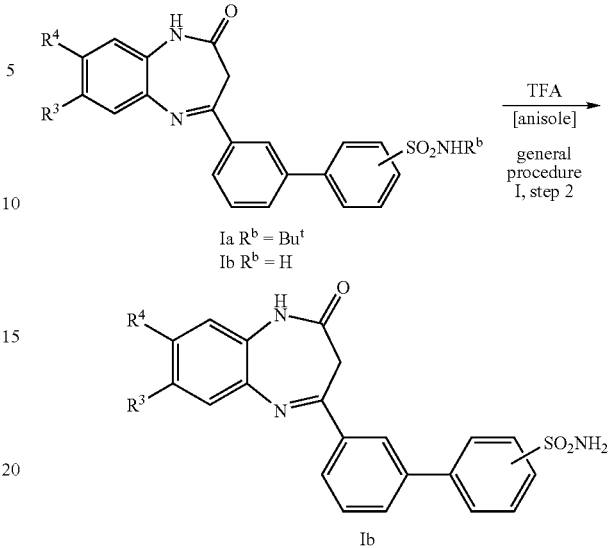

According to scheme A, compounds of general formula I, in which R", $R^3$ and $R^4$ are as described above, can be prepared from compounds of general formula II [(2-amino-phenyl)-carbamic acid tert-butyl ester] and β-ketoesters of general formula III via an acylation-deprotection-cyclization sequence to produce compounds of general formula V, in which the bromide or iodide can be reacted with boronic acid derivatives of general formula VI to give compounds of general formula Ia (compounds of formula I wherein $R^1$ is H and $R^2$ is —S(O)$_2$—NR$^a$R$^b$ or $R^2$ is H and $R^1$ is —S(O)$_2$—NR$^a$R$^b$, $R^a$ is and $R^b$ is $C_{1-6}$-alkyl, e.g. Bu$^t$). or directly of general formula Ib (compounds of formula I wherein $R^1$ is H and $R^2$ is —S(O)$_2$—NR$^a$R$^b$ or $R^2$ is H and $R^1$ is —S(O)$_2$—NR$^a$R$^b$ and $R^a$ and $R^b$ are both H).

For example reacting compounds of general formula II, in which $R^3$ and $R^4$ are as described above, with a β-ketoester of general formula III, in which R can be $C_{1-6}$-alkyl, preferably tert-butyl or ethyl, and X is either bromine or iodine, in an inert solvent such as toluene or xylene at elevated temperatures, preferably between 80° C. and 160° C. gives rise to the corresponding β-ketoamides of general formula IV.

The preparation of the corresponding (2-amino-phenyl)-carbamic acid tert-butyl esters of general formula II, in which $R^3$ and $R^4$ are as described above, are extensively described and can be found in the following patents: WO 2001029011 (CAN 134:311234), WO 2001029012 (CAN 134:311235), WO 2002083652 (CAN 137:325447), WO 2002083665 (CAN 137:325438) and WO 2003066623 (CAN 139:180090). The respective CAS numbers and references of the compounds used are given in the experimental part.

The ethyl or tert-butyl 3-aryl-3-oxo-propionates of general formula III (with X being bromide or iodide) are either commercially available (R=Et, X=I: CAS-no. [68332-33-2], R=Et, X=Br: CAS-no. [21575-91-7]) or can be prepared by numerous methods known to someone skilled in the art. A selection of methods is as follows:

The ethyl or tert-butyl 3-aryl-3-oxo-propionates of general formula III can be prepared from the aryl acid chlorides and ethyl or tert-butyl malonate potassium salt [CAS-no. 6148-64-7 and 75486-33-8] with $Et_3N$ and $MgCl_2$ in $CH_3CN$ at 0° C. to 23° C. according to Synthesis 1993, 290. If the free aryl carboxylic acid is employed in this reaction, it is activated by treatment with ethyl chloroformate and Et₃N in THF/CH₃CN at 0° C. prior to reaction with the malonate salt.

The tert-butyl 3-aryl-3-oxo-propionates of general formula III can alternatively be prepared from the 1° alkyl aryl esters of general formula VIII by treatment with lithium tert-butyl acetate [prepared by treatment of tert-butyl acetate with lithium diisopropylamide in THF at −78° C.] in the presence of lithium tert-butoxide according to Synthesis 1985, 45. If the product contains residual starting material after workup, thus could be removed by selective saponification with LiOH in THF/MeOH/H₂O at 23° C.

Yet another method of preparing the tert-butyl 3-(3-bromo- or iodo-phenyl)-3-oxo-propionates of general formula III is depicted in scheme B, which utilizes excess lithium hexamethyldisilazide as base in the condensation reaction of tert-butyl acetate and 1° alkyl aryl esters of general formula VIII (described in detail in general procedure III).

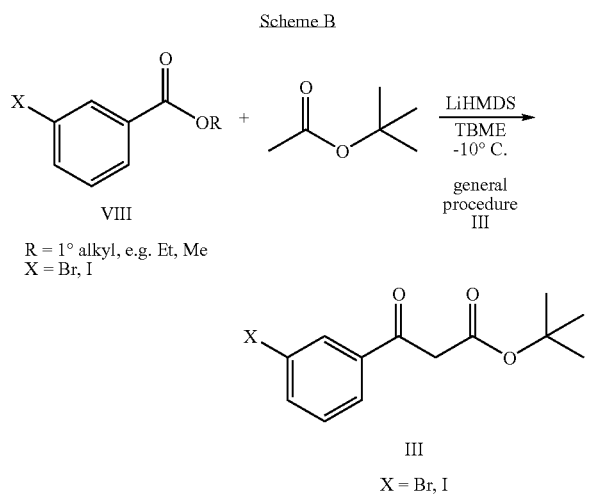

Scheme B

VIII
R = 1° alkyl, e.g. Et, Me
X = Br, I general procedure III

III
X = Br, I

After achieving the formation of the β-ketoamides of general formula IV, cleaving the BOC protecting group and concomitant cyclization of the deprotected compound yields the compounds of general formula V (4-(3-bromo- or iodo-phenyl)-1,3-dihydro-benzo[b][1,4]diazepin-2-ones). The deprotection-cyclization step can be carried out by treating the compounds of general formula IV with for example a Bronsted acid such as trifluoroacetic acid in an inert solvent such as dichloromethane (DCM). The reaction is preferably carried out at temperatures between 0° C. and 50° C. It may be advantageous to use also anisole as a carbocation scavenger in the reaction mixture.

The replacement of the bromide or iodide in compounds of the general formula V with a phenyl group bearing a sulfonamide residue in either 3- or 4-position can be achieved by so called Suzuki-Miyaura-coupling with a boronic acid derivative of the general formula VI. The reaction is carried out in an organic solvent, e.g. 1,2-dimethoxyethane or 1,4-dioxane, at temperatures between 60 and 110° C. in the presence of a base, e.g. aqueous solution of sodium carbonate, and a palladium catalyst, e.g. Pd(PPh₃)₄. Many variations of these reaction conditions are known to someone skilled in the art and will lead to the desired compounds of general formula Ia or directly to the compounds of the general formula I.

In the case where R=tert-butyl in compounds of the general formula Ia, the tert-butyl group can be removed by treatment with a Bronsted acid such as trifluoroacetic acid, methanesulfonic acid or sulphuric acid at temperatures between 0 and 50° C. to give the desired compounds of the general formula I. It may be advantageous to use also anisole as a carbocation scavenger in the reaction mixture.

Synthesis of the 4-(3-Bromo- or iodo-phenyl)-1,3-dihydro-benzo[b][1,4]diazepin-2-ones General Procedure I Step 1: A mixture of the (2-amino-phenyl)-carbamic acid tert-butyl ester of general formula II (1.0 mmol) and excess (1.2-1.5 mmol) of the tert-butyl of ethyl 3-(3-bromo- or iodo-phenyl)-3-oxo-propionate of general formula III was refluxed in toluene (8-12 mL) until tlc indicated complete consumption of the amine. The solution was allowed to cool to 23° C., whereupon the product generally crystallized (in cases where crystallization failed to appear it was induced by addition of n-heptane). The solid was filtered off, washed with ether or mixtures of ether/hexane and dried in vacuum to give the {2-[3-(3-bromo- or iodo-phenyl)-3-oxo-propionylamino]-phenyl}-carbamic acid tert-butyl ester of general formula IV, which was used directly in the following step or—if necessary—was purified by recrystallization or by silica gel column chromatography with n-heptane and ethyl acetate.

Step 2: A suspension of the above described {2-[3-(3-bromo- or iodo-phenyl)-3-oxo-propionylamino]-phenyl}-carbamic acid tert-butyl ester of general formula IV (1.0 mmol) in dichloromethane (DCM) (5 mL) [anisole (5-15 mmol) can be added if necessary] was treated with trifluoroacetic acid (TFA) (0.5-5.0 mL) at 0° C. and stirring was continued at 23° C. until tlc indicated complete consumption of the starting material. The solvent was removed in vacuum, the residue treated with little ether, whereupon it crystallized. The solid was stirred with sat. NaHCO₃-sol., filtered, washed with H₂O and ether or mixtures of ether/hexane and was dried to give the 4-(3-bromo- or iodo-phenyl)-1,3-dihydro-benzo[b][1,4]diazepin-2-one of general formula V, which—if necessary—can be purified by silica gel column chromatography with n-heptane/ethyl acetate and/or crystallization from THF/DCM/ether/n-heptane.

For the conversion of compounds of general formula Ia to compounds of general formula I the same procedure as in general procedure I step 2 applies, but preferably with the use of less or even without any DCM as solvent.

General Procedure II

To a stirred mixture of a compound of formula V (1 eq), a boronic acid derivative of general formula VI (1.1 eq) and tetrakis(triphenylphosphine)palladium (0.03 eq) in an organic solvent (e.g. 1,2-dimethoxy-ethane) is added at room temperature aqueous 1 M sodium carbonate solution (2.5 eq), the reaction mixture is heated at 80 to 90° C. for around 18 h, cooled, poured into ice-water and extracted two times with ethyl acetate. The combined organic layers are washed two times with brine, dried (e.g. MgSO₄) and evaporated. The crude product is further purified by flash chromatography on silica gel (ethyl acetate/n-heptane) and crystallization (e.g. dichloromethane/diethyl ether/n-heptane) to give compounds of general formulae Ia or Ib.

Synthesis of tert-butyl 3-(3-bromo- or iodo-phenyl)-3-oxo-propionates

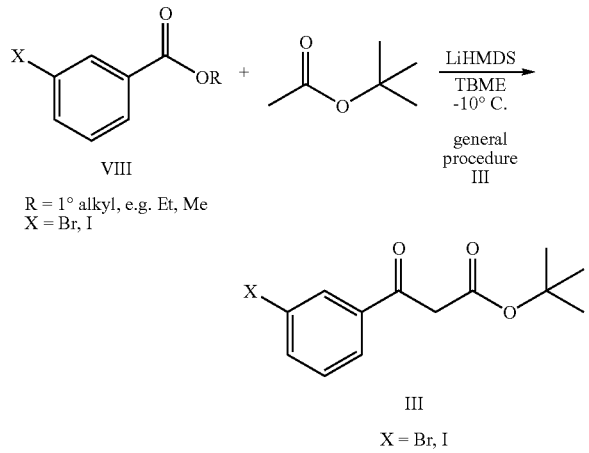

R = 1° alkyl, e.g. Et, Me
X = Br, I

X = Br, I

General Procedure III

To a solution of hexamethyldisilizane (2.4 eq.) in tert-butyl methyl ether (2 M) at 0° C. was dropwise added n-butyllithium (2.35 eq.) the mixture was stirred at 0° C. for 10 min, then added via syringe into a solution of 1° alkyl (e.g. methyl or ethyl) aryl esters of general formula VIII (1.0 eq.) and tert-butyl acetate (1.0-1.1 eq.) in tert-butyl methyl ether (0.4 M of the ester) at −10° C. Stirring was continued at −10 to 0° C. for 45 min, poured into ice water, extracted with tert-butyl methyl ether, washed with water and 1 M HCl, dried over $Na_2SO_4$. Removal of the solvent in vacuum left a crude product, which was either used directly or purified by silica gel column chromatography with n-heptane/ethyl acetate to give the tert-butyl 3-aryl-3-oxo-propionates of general formula III.

Example A.1

3-(3-Bromo-phenyl)-3-oxo-propionic acid tert-butyl ester

Prepared from hexamethyldisilizane (16.5 mL, 79 mmol) and n-BuLi (48.4 mL, 77 mmol) in TBME (40 mL), then commercially available ethyl 3-bromobenzoate (7.55 g, 33 mmol) and tert-butyl acetate (4.86 mL, 36 mmol) in TBME (80 mL) according to the general procedure III. Obtained as a light yellow oil (9.934 g, 101%; 95% purity).

Example B.1

4-(3-Bromo-phenyl)-7-methyl-8-trifluoromethyl-1,3-dihydro-benzo[b][1,4]diazepin-2-one 1.) {2-[3-(3-Bromo-phenyl)-3-oxo-propionylamino]-5-methyl-4-trifluoromethyl-phenyl}-carbamic acid tert-butyl ester Prepared from (2-amino-5-methyl-4-trifluoromethyl-phenyl)-carbamic acid tert-butyl ester [CAS-no. 473537-79-0; cf. WO200283665, WO200366623] (2.90 g, 10 mmol) and 3-(3-bromo-phenyl)-3-oxo-propionic acid tert-butyl ester (Example A.1) (3.89 g, 13 mmol) in toluene (100 mL) according to general procedure I step 1. Obtained as a white solid (3.59 g, 70%). MS (ISN) 513.3 [(M−H)$^-$] and 515 [(M+2−H)$^-$]; mp 180-182° C.

2.) The title compound was prepared from the above described {2-[3-(3-bromo-phenyl)-3-oxo-propionylamino]-5-methyl-4-trifluoromethyl-phenyl}-carbamic acid tert-butyl ester (3.50 g, 6.79 mmol) and TFA (20 mL) in DCM (60 mL) according to general procedure I step 2. Obtained as a light yellow solid (1.79 g, 64%). MS (ISP) 397.1 [(M+H)$^+$] and 399.1 [(M+2+H)$^+$]; mp 198-202° C.

Example B.2

4-(3-Bromo-phenyl)-8-trifluoromethyl-1,3-dihydro-benzo[b][1,4]diazepin-2-one

1.) {2-[3-(3-Bromo-phenyl)-3-oxo-propionylamino]-4-trifluoromethyl-phenyl}-carbamic acid tert-butyl ester Prepared from (2-amino-4-trifluoromethyl-phenyl)-carbamic acid tert-butyl ester [CAS-no. 579474-48-9; cf. WO200366623] (1.381 g, 5 mmol) and 3-(3-bromo-phenyl)-3-oxo-propionic acid tert-butyl ester (Example A.1) (1.496 g, 5 mmol) in toluene (10 mL) according to general procedure I step 1. Obtained as a white solid (1.152 g, 46%). MS (ISP) 500.9 [(M+H)$^+$] and 502.8 [(M+2+H)$^+$].

2.) The title compound was prepared from the above described {2-[3-(3-bromo-phenyl)-3-oxo-propionylamino]-4-trifluoromethyl-phenyl}-carbamic acid tert-butyl ester (1.152 g, 2.30 mmol) and TFA (10 mL) according to general procedure I step 2. Obtained as a light yellow solid (0.730 g, 82%). MS (ISP) 383.0 [(M+H)$^+$] and 385.0 [(M+2+H)$^+$].

Example B.3

4-(3-Bromo-phenyl)-7-ethoxy-8-trifluoromethyl-1,3-dihydro-benzo[b][1,4]diazepin-2-one 1.) {2-[3-(3-Bromo-phenyl)-3-oxo-propionylamino]-5-ethoxy-4-trifluoromethyl-phenyl}-carbamic acid tert-butyl ester Prepared from (2-amino-5-ethoxy-4-trifluoromethyl-phenyl)-carbamic acid tert-butyl ester [CAS-no. 473537-75-6; cf. WO200283665, WO200366623] (1.602 g, 5 mmol) and 3-(3-bromo-phenyl)-3-oxo-propionic acid tert-butyl ester (Example A.1) (1.496 g, 5 mmol) in toluene (10 mL) according to general procedure I step 1. Obtained as a white solid (1.459 g, 54%). MS (ISP) 544.8 [(M+H)$^+$] and 546.7 [(M+2+H)$^+$].

2.) The title compound was prepared from the above described {2-[3-(3-bromo-phenyl)-3-oxo-propionylamino]-5-ethoxy-4-trifluoromethyl-phenyl}-carbamic acid tert-butyl ester (1.459 g, 2.675 mmol) and TFA (10 mL) according to general procedure I step 2. Obtained as a light yellow solid (0.940 g, 82%). MS (ISP) 427.1 [(M+H)$^+$] and 429.1 [(M+2+H)$^+$].

Example B.4

4-(3-Bromo-phenyl)-8-(2-fluoro-phenyl)-1,3-dihydro-benzo[b][1,4]diazepin-2-one

1.) {3-[3-(3-Bromo-phenyl)-3-oxo-propionylamino]-2'-fluoro-biphenyl-4-yl}-carbamic acid tert-butyl ester Prepared from (3-Amino-2'-fluoro-biphenyl-4-yl)-carbamic acid tert-butyl ester [CAS-no. 335255-65-7; cf. WO20010426, WO200366623] (1.153 g, 3.814 mmol) and 3-(3-bromo-phenyl)-3-oxo-propionic acid tert-butyl ester (Example A.1) (1.141 g, 3.814 mmol) in toluene (10 mL) according to general procedure I step 1. Obtained as an off-white solid (2.15 g, 107%, 90% purity). MS (ISP) 526.8 [(M+H)$^+$] and 528.7 [(M+2+H)$^+$].

2.) The title compound was prepared from the above described {3-[3-(3-bromo-phenyl)-3-oxo-propionylamino]-2'-fluoro-biphenyl-4-yl}-carbamic acid tert-butyl ester (2.15 g, 4.076 mmol, 90% purity) and TFA (15 mL) according to general procedure I step 2. Obtained as a light yellow solid (1.25 g, 75%). MS (ISP) 409.0 [(M+H)$^+$] and 411.0 [(M+2+H)$^+$].

Example B.5

4-(3-Bromo-phenyl)-7-dimethylamino-8-trifluoromethyl-1,3-dihydro-benzo[b][1,4]diazepin-2-one 1.) {2-[3-(3-Bromo-phenyl)-3-oxo-propionylamino]-5-dimethylamino-4-trifluoromethyl-phenyl}-carbamic acid tert-butyl ester Prepared from (2-amino-5-dimethylamino-4-trifluoromethyl-phenyl)-carbamic acid tert-butyl ester [CAS-No. 473547-60-3; cf. WO200283665, WO200366623] (1.50 g, 4.7 mmol) and 3-(3-bromo-phenyl)-3-oxo-propionic acid tert-butyl ester (Example A.1) (1.69 g, 5.65 mmol) in toluene (60 mL) according to general procedure I step 1. Obtained as pink foam (2.2 g, 86%).

2.) The title compound was prepared from the above described {2-[3-(3-bromo-phenyl)-3-oxo-propionylamino]-5-dimethylamino-4-trifluoromethyl-phenyl}-carbamic acid tert-butyl ester (2.2 g, 4.04 mmol) and TFA (15 mL) in DCM (45 mL) according to general procedure I step 2. Obtained as an off-white solid (1.61 g, 93%). MS (ISP) 426.0 [(M+H)$^+$]; mp 193° C. (dec).

Example B.6

4-(3-Bromo-phenyl)-7-(isobutyl-methyl-amino)-8-trifluoromethyl-1,3-dihydro-benzo[b][1,4]diazepin-2-one 1.) {2-[3-(3-Bromo-phenyl)-3-oxo-propionylamino]-5-(isobutyl-methyl-amino)-4-trifluoromethyl-phenyl}-carbamic acid tert-butyl ester Prepared from [2-amino-5-(isobutyl-methyl-amino)-4-trifluoromethyl-phenyl]-carbamic acid tert-butyl ester [CAS-No. 473547-90-9; cf. WO200283665, WO200366623] (0.96 g, 2.66 mmol) and 3-(3-bromo-phenyl)-3-oxo-propionic acid tert-butyl ester (Example A.1) (0.95 g, 3.18 mmol) in toluene (35 mL) according to general procedure I step 1. Obtained as brown foam (1.01 g, 65%).

2.) The title compound was prepared from the above described {2-[3-(3-bromo-phenyl)-3-oxo-propionylamino]-5-(isobutyl-methyl-amino)-4-trifluoromethyl-phenyl}-carbamic acid tert-butyl ester (1.01 g, 1.72 mmol) and TFA (6.5 mL) in DCM (20 mL) according to general procedure I step 2. Obtained as a white solid (0.65 g, 81%). MS (ISP) 468.0 [(M+H)$^+$]; mp 186° C. (dec).

Example B.7

4-(3-Bromo-phenyl)-7-isobutylamino-8-trifluoromethyl-1,3-dihydro-benzo[b][1,4]diazepin-2-one 1.) {2-[3-(3-Bromo-phenyl)-3-oxo-propionylamino]-5-isobutylamino-4-trifluoromethyl-phenyl}-carbamic acid tert-butyl ester Prepared from (2-amino-5-isobutylamino-4-trifluoromethyl-phenyl)-carbamic acid tert-butyl ester [CAS-No. 473547-95-4; cf. WO200283665, WO200366623] (1.51 g, 4.35 mmol) and 3-(3-bromo-phenyl)-3-oxo-propionic acid tert-butyl ester (Example A.1) (1.56 g, 5.21 mmol) in toluene (60 mL) according to general procedure I step 1. Obtained as a light yellow solid (1.03 g, 42%).

2.) The title compound was prepared from the above described {2-[3-(3-bromo-phenyl)-3-oxo-propionylamino]-5-isobutylamino-4-trifluoromethyl-phenyl}-carbamic acid tert-butyl ester (1.03 g, 1.8 mmol) and TFA (7 mL) in DCM (20 mL) according to general procedure I step 2. Obtained as a light yellow solid (0.75 g, 92%). MS (ISP) 454.3 [(M+H)$^+$]; mp 217° C. (dec).

Example 1

3'-(8-Methyl-4-oxo-7-trifluoromethyl-4,5-dihydro-3H-benzo[b][1,4]diazepin-2-yl)-biphenyl-4-sulfonic acid amide The title compound was prepared from 4-(3-bromo-phenyl)-7-methyl-8-trifluoromethyl-1,3-dihydro-benzo[b][1,4]diazepin-2-one (Example B.1) (200 mg, 0.50 mmol) and commercially available 4-(4,4,5,5-tetramethyl-1,3,2-dioxaborolan-2-yl)-benzenesulfonamide [CAS-no. 214360-51-7] (170 mg, 0.60 mmol) according to the general procedure II. Obtained as a white solid (165 mg, 69%). MS (ISP) 473.9 [(M+H)$^+$]; mp>260° C.

Example 2

3'-(8-Methyl-4-oxo-7-trifluoromethyl-4,5-dihydro-3H-benzo[b][1,4]diazepin-2-yl)-biphenyl-3-sulfonic acid tert-butylamide The title compound was prepared from 4-(3-bromo-phenyl)-7-methyl-8-trifluoromethyl-1,3-dihydro-benzo[b][1,4]diazepin-2-one (Example B.1) (200 mg, 0.50 mmol) and commercially available 3-tert-butylsulfamoyl-benzeneboronic acid [CAS-no. 221290-14-8] (155 mg, 0.60 mmol) according to the general procedure II. Obtained as a light yellow solid (275 mg, 97%). MS (ISP) 530.1 [(M+H)$^+$]; mp 133° C. (dec).

Example 3

3'-(8-Methyl-4-oxo-7-trifluoromethyl-4,5-dihydro-3H-benzo[b][1,4]diazepin-2-yl)-biphenyl-3-sulfonic acid amide The title compound was prepared from 3'-(8-methyl-4-oxo-7-trifluoromethyl-4,5-dihydro-3H-benzo[b][1,4]diazepin-2-yl)-biphenyl-3-sulfonic acid tert-butylamide (Example 2) (220 mg, 0.39 mmol) and TFA (5 mL) in DCM (1 mL) according to the general procedure I step 2. Obtained as a light yellow solid (136 mg, 73%). MS (ISP) 473.9 [(M+H)$^+$]; mp 235-239° C. (dec).

Example 4

3'-(4-Oxo-7-trifluoromethyl-4,5-dihydro-3H-benzo[b][1,4]diazepin-2-yl)-biphenyl-3-sulfonic acid tert-butylamide The title compound was prepared from 4-(3-bromo-phenyl)-8-trifluoromethyl-1,3-dihydro-benzo[b][1,4]diazepin-2-one (Example B.2) (200 mg, 0.50 mmol) and commercially available 3-tert-butylsulfamoyl-benzeneboronic acid [CAS-no. 221290-14-8] (161 mg, 0.60 mmol) according to the general procedure II. Obtained as an off-white solid (31 mg, 12%). MS (ISP) 515.9 [(M+H)$^+$]; mp 179-181° C.

Example 5

3'-(4-Oxo-7-trifluoromethyl-4,5-dihydro-3H-benzo[b][1,4]diazepin-2-yl)-biphenyl-4-sulfonic acid tert-butylamide The title compound was prepared from 4-(3-bromo-phenyl)-8-trifluoromethyl-1,3-dihydro-benzo[b][1,4]diazepin-2-one (Example B.2) (200 mg, 0.50 mmol) and commercially available 4-tert-butylsulfamoyl-benzeneboronic acid [CAS-no. 208516-15-8] (161 mg, 0.60 mmol) according to the general procedure II. Obtained as a white solid (125 mg, 46%). MS (ISP) 515.9 [(M+H)$^+$]; mp 229-233° C.

Example 6

3'-(8-Ethoxy-4-oxo-7-trifluoromethyl-4,5-dihydro-3H-benzo[b][1,4]diazepin-2-yl)-biphenyl-3-sulfonic acid tert-butylamide The title compound was prepared from 4-(3-bromo-phenyl)-7-ethoxy-8-trifluoromethyl-1,3-dihydro-benzo[b][1,4]diazepin-2-one (Example B.3) (200 mg, 0.50 mmol) and commercially available 3-tert-butylsulfamoyl-benzeneboronic acid [CAS-no. 221290-14-8] (144 mg, 0.55 mmol) according to the general procedure II. Obtained as an off-white solid (169 mg, 65%). MS (ISP) 559.7 [(M+H)$^+$]; mp 215-218° C.

Example 7

3'-(8-Ethoxy-4-oxo-7-trifluoromethyl-4,5-dihydro-3H-benzo[b][1,4]diazepin-2-yl)-biphenyl-4-sulfonic acid tert-butylamide The title compound was prepared from 4-(3-bromo-phenyl)-7-ethoxy-8-trifluoromethyl-1,3-dihydro-benzo[b][1,4]diazepin-2-one (Example B.3) (200 mg, 0.50 mmol) and commercially available 4-tert-butylsulfamoyl-benzeneboronic acid [CAS-no. 208516-15-8] (144 mg, 0.55 mmol) according to the general procedure II. Obtained as a white solid (164 mg, 63%). MS (ISP) 559.7 [(M+H)$^+$]; mp>260° C.

Example 8

3'-(4-Oxo-7-trifluoromethyl-4,5-dihydro-3H-benzo[b][1,4]diazepin-2-yl)-biphenyl-3-sulfonic acid amide The title compound was prepared from 3'-(4-oxo-7-trifluoromethyl-4,5-dihydro-3H-benzo[b][1,4]diazepin-2-yl)-biphenyl-3-sulfonic acid tert-butylamide (Example 4) (177 mg, 0.3 mmol) and TFA (5 mL) according to the general procedure I step 2. Obtained as an off-white solid (122 mg, 77%). MS (ISP) 460.0 [(M+H)$^+$]; mp 170° C. (dec).

Example 9

3'-(4-Oxo-7-trifluoromethyl-4,5-dihydro-3H-benzo[b][1,4]diazepin-2-yl)-biphenyl-4-sulfonic acid amide The title compound was prepared from 3'-(4-oxo-7-trifluoromethyl-4,5-dihydro-3H-benzo[b][1,4]diazepin-2-yl)-biphenyl-4-sulfonic acid tert-butylamide (Example 5) (235 mg, 0.5 mmol) and TFA (5 mL) according to the general procedure I step 2. Obtained as a yellow solid (122 mg, 58%). MS (ISP) 460.1 [(M+H)$^+$]; mp 195-210° C. (dec).

Example 10

3'-(8-Ethoxy-4-oxo-7-trifluoromethyl-4,5-dihydro-3H-benzo[b][1,4]diazepin-2-yl)-biphenyl-3-sulfonic acid amide The title compound was prepared from 3'-(8-ethoxy-4-oxo-7-trifluoromethyl-4,5-dihydro-3H-benzo[b][1,4]diazepin-2-yl)-biphenyl-3-sulfonic acid tert-butylamide (Example 6) (238 mg, 0.4 mmol) and TFA (5 mL) according to the general procedure I step 2. Obtained as an off-white solid (147 mg, 69%). MS (ISP) 503.8 [(M+H)$^+$]; mp 210-220° C. (dec).

Example 11

3'-(8-Ethoxy-4-oxo-7-trifluoromethyl-4,5-dihydro-3H-benzo[b][1,4]diazepin-2-yl)-biphenyl-4-sulfonic acid amide The title compound was prepared from 3'-(8-ethoxy-4-oxo-7-trifluoromethyl-4,5-dihydro-3H-benzo[b][1,4]diazepin-2-yl)-biphenyl-4-sulfonic acid tert-butylamide (Example 7) (205 mg, 0.4 mmol) and TFA (5 mL) according to the general procedure I step 2. Obtained as an off-white solid (94 mg, 51%). MS (ISP) 503.8 [(M+H)$^+$]; mp 245-250° C. (dec).

Example 12

3'-(8-Dimethylamino-4-oxo-7-trifluoromethyl-4,5-dihydro-3H-benzo[b][1,4]diazepin-2-yl)-biphenyl-4-sulfonic acid amide 1.) 3'-(8-Dimethylamino-4-oxo-7-trifluoromethyl-4,5-dihydro-3H-benzo[b][1,4]diazepin-2-yl)-biphenyl-4-sulfonic acid tert-butylamide: Prepared from 4-(3-bromo-phenyl)-7-dimethylamino-8-trifluoromethyl-1,3-dihydro-benzo[b][1,4]diazepin-2-one (Example B.5) (213 mg, 0.5 mmol) and commercially available 4-tert-butylsulfamoyl-benzeneboronic acid (154 mg, 0.6 mmol) according to the general procedure II. Obtained as a yellow solid (132 mg), which was subsequently deprotected.

2.) The title compound was prepared from the above described 3'-(8-dimethylamino-4-oxo-7-trifluoromethyl-4,5-dihydro-3H-benzo[b][1,4]diazepin-2-yl)-biphenyl-4-sulfonic acid tert-butylamide (132 mg) and TFA (3 mL) according to the general procedure I step 2. Obtained as a white solid (55 mg, 22%). MS (ISP) 501.4 [(M–H)$^-$]; mp 246° C. (dec).

Example 13

3'-(8-Dimethylamino-4-oxo-7-trifluoromethyl-4,5-dihydro-3H-benzo[b][1,4]diazepin-2-yl)-biphenyl-3-sulfonic acid amide 1.) 3'-(8-Dimethylamino-4-oxo-7-trifluoromethyl-4,5-dihydro-3H-benzo[b][1,4]diazepin-2-yl)-biphenyl-3-sulfonic acid tert-butylamide: Prepared from 4-(3-bromo-phenyl)-7-dimethylamino-8-trifluoromethyl-1,3-dihydro-benzo[b][1,4]diazepin-2-one (Example B.5) (213 mg, 0.5 mmol) and commercially available 3-tert-butylsulfamoyl-benzeneboronic acid (154 mg, 0.6 mmol) according to the general procedure II. Obtained as a yellow solid (130 mg), which was subsequently deprotected.

2.) The title compound was prepared from the above described 3'-(8-dimethylamino-4-oxo-7-trifluoromethyl-4, 5-dihydro-3H-benzo[b][1,4]diazepin-2-yl)-biphenyl-3-sulfonic acid tert-butylamide (130 mg) and TFA (3 mL) according to the general procedure I step 2. Obtained as a light yellow solid (40 mg, 16%). MS (ISN) 501.4 [(M−H)$^−$]; mp 258° C. (dec).

Example 14

3'-[8-(Isobutyl-methyl-amino)-4-oxo-7-trifluoromethyl-4,5-dihydro-3H-benzo[b][1,4]diazepin-2-yl]-biphenyl-4-sulfonic acid amide 1.) 3'-[8-(Isobutyl-methyl-amino)-4-oxo-7-trifluoromethyl-4,5-dihydro-3H-benzo[b][1,4]diazepin-2-yl]-biphenyl-4-sulfonic acid tert-butylamide: Prepared from 4-(3-bromo-phenyl)-7-(isobutyl-methyl-amino)-8-trifluoromethyl-1,3-dihydro-benzo[b][1,4]diazepin-2-one (Example B.6) (234 mg, 0.5 mmol) and commercially available 4-tert-butylsulfamoyl-benzeneboronic acid (154 mg, 0.6 mmol) according to the general procedure II. Obtained as a yellow solid (250 mg), which was subsequently deprotected.

2.) The title compound was prepared from the above described 3'-[8-(isobutyl-methyl-amino)-4-oxo-7-trifluoromethyl-4,5-dihydro-3H-benzo[b][1,4]diazepin-2-yl]-biphenyl-4-sulfonic acid tert-butylamide (250 mg) and TFA (5 mL) according to the general procedure I step 2. Obtained as a white solid (107 mg, 39%). MS (ISN) 543.5 [(M−H)$^−$]; mp 236° C. (dec).

Example 15

3'-[8-(Isobutyl-methyl-amino)-4-oxo-7-trifluoromethyl-4,5-dihydro-3H-benzo[b][1,4]diazepin-2-yl]-biphenyl-3-sulfonic acid amide 1.) 3'-[8-(Isobutyl-methyl-amino)-4-oxo-7-trifluoromethyl-4,5-dihydro-3H-benzo[b][1,4]diazepin-2-yl]-biphenyl-3-sulfonic acid tert-butylamide: Prepared from 4-(3-bromo-phenyl)-7-(isobutyl-methyl-amino)-8-trifluoromethyl-1,3-dihydro-benzo[b][1,4]diazepin-2-one (Example B.6) (234 mg, 0.5 mmol) and commercially available 3-tert-butylsulfamoyl-benzeneboronic acid (154 mg, 0.6 mmol) according to the general procedure II. Obtained as a yellow solid (250 mg), which was subsequently deprotected.

2.) The title compound was prepared from the above described 3'-[8-(isobutyl-methyl-amino)-4-oxo-7-trifluoromethyl-4,5-dihydro-3H-benzo[b][1,4]diazepin-2-yl]-biphenyl-3-sulfonic acid tert-butylamide (250 mg) and TFA (5 mL) according to the general procedure I step 2. Obtained as a light yellow solid (69 mg, 25%). MS (ISN) 543.5 [(M−H)$^−$]; mp 232° C. (dec).

Example 16

3'-[7-(2-Fluoro-phenyl)-4-oxo-4,5-dihydro-3H-benzo[b][1,4]diazepin-2-yl]-biphenyl-4-sulfonic acid amide 1.) 3'-[7-(2-Fluoro-phenyl)-4-oxo-4,5-dihydro-3H-benzo[b][1,4]diazepin-2-yl]-biphenyl-4-sulfonic acid tert-butylamide: Prepared from 4-(3-bromo-phenyl)-8-(2-fluoro-phenyl)-1,3-dihydro-benzo[b][1,4]diazepin-2-one (Example B.4) (600 mg, 1.467 mmol) and commercially available 4-tert-butylsulfamoyl-benzeneboronic acid [CAS-no. 208516-15-8] (283 mg, 2.2 mmol) according to the general procedure II. Obtained as a brown oil (330 mg, 35%; 45% purity). MS (ISP) 542.2 [(M+H)$^+$].

2.) The title compound was prepared from the above described 3'-[7-(2-fluoro-phenyl)-4-oxo-4,5-dihydro-3H-benzo[b][1,4]diazepin-2-yl]-biphenyl-4-sulfonic acid tert-butylamide (310 mg, 0.573 mmol, 45% purity) and TFA (5 mL) according to the general procedure I step 2. Obtained as an off-white solid (20 mg, 13%, 80% purity). MS (ISP) 486.0 [(M+H)$^+$]; mp 240-250° C. (dec).

Example 17

3'-[7-(2-Fluoro-phenyl)-4-oxo-4,5-dihydro-3H-benzo[b][1,4]diazepin-2-yl]-biphenyl-3-sulfonic acid amide 1.) 3'-[7-(2-Fluoro-phenyl)-4-oxo-4,5-dihydro-3H-benzo[b][1,4]diazepin-2-yl]-biphenyl-3-sulfonic acid tert-butylamide: Prepared from 4-(3-bromo-phenyl)-8-(2-fluoro-phenyl)-1,3-dihydro-benzo[b][1,4]diazepin-2-one (Example B.4) (400 mg, 0.978 mmol) and commercially available 3-tert-butylsulfamoyl-benzeneboronic acid [CAS-no. 221290-14-8] (377 mg, 1.467 mmol) according to the general procedure II. Obtained as an off-white solid (430 mg, 81%). MS (ISP) 541.9 [(M+H)$^+$].

2.) The title compound was prepared from the above described 3'-[7-(2-fluoro-phenyl)-4-oxo-4,5-dihydro-3H-benzo[b][1,4]diazepin-2-yl]-biphenyl-3-sulfonic acid tert-butylamide (430 mg, 0.795 mmol) and TFA (5 mL) according to the general procedure I step 2. Obtained as a white solid (380 mg, 99%). MS (ISP) 486.0 [(M+H)$^+$]; mp 230-232° C.

Example 18

3'-(8-Isobutylamino-4-oxo-7-trifluoromethyl-4,5-dihydro-3H-benzo[b][1,4]diazepin-2-yl)-biphenyl-4-sulfonic acid amide 1.) 3'-(8-Isobutylamino-4-oxo-7-trifluoromethyl-4,5-dihydro-3H-benzo[b][1,4]diazepin-2-yl)-biphenyl-4-sulfonic acid tert-butylamide: Prepared from 4-(3-bromo-phenyl)-7-isobutylamino-8-trifluoromethyl-1,3-dihydro-benzo[b][1,4]diazepin-2-one (Example B.7) (227 mg, 0.5 mmol) and commercially available 4-tert-butylsulfamoyl-benzeneboronic acid (154 mg, 0.6 mmol) according to the general procedure II. Obtained as a yellow solid (275 mg), which was subsequently deprotected.

2.) The title compound was prepared from the above described 3'-(8-isobutylamino-4-oxo-7-trifluoromethyl-4,5-dihydro-3H-benzo[b][1,4]diazepin-2-yl)-biphenyl-4-sulfonic acid tert-butylamide (275 mg) and TFA (6 mL) according to the general procedure I step 2. Obtained as a yellow solid (126 mg, 47%). MS (ISN) 529.4 [(M−H)$^−$]; mp 251° C. (dec).

Example 19

3'-(8-Isobutylamino-4-oxo-7-trifluoromethyl-4,5-dihydro-3H-benzo[b][1,4]diazepin-2-yl)-biphenyl-3-sulfonic acid amide 1.) 3'-(8-Isobutylamino-4-oxo-7-trifluoromethyl-4,5-dihydro-3H-benzo[b][1,4]diazepin-2-yl)-biphenyl-3-sulfonic acid tert-butylamide: Prepared from 4-(3-bromo-phenyl)-7-isobutylamino-8-trifluoromethyl-1,3-dihydro-benzo[b][1,4]diazepin-2-one (Example B.7) (227 mg, 0.5 mmol) and commercially available 3-tert-butylsulfamoyl-benzeneboronic acid (154 mg, 0.6 mmol) according to the general procedure II. Obtained as a yellow solid (275 mg), which was subsequently deprotected.

2.) The title compound was prepared from the above described 3'-(8-isobutylamino-4-oxo-7-trifluoromethyl-4,5-dihydro-3H-benzo[b][1,4]diazepin-2-yl)-biphenyl-3-sulfonic acid tert-butylamide (275 mg) and TFA (6 mL) according to the general procedure I step 2. Obtained as a yellow solid (172 mg, 65%). MS (ISN) 529.4 [(M−H)⁻]; mp 251° C. (dec).

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The following Examples illustrate the present invention without limiting it. All temperatures are given in degrees Celsius.

Example A

Tablets of the following composition can be manufactured in the usual manner:

|  | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition can be manufactured:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch can be firstly mixed in a mixer and then in a comminuting machine. The mixture can be returned to the mixer, the talc can be added thereto and mixed thoroughly. The mixture can be filled by machine into hard gelatin capsules.

The invention claimed is:
1. A compound of formula (I):

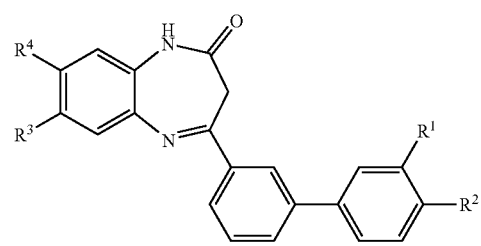

wherein:
R¹ is H and R² is —S(O)₂—NRᵃRᵇ or R² is H and R¹ is —S(O)₂—NRᵃRᵇ;
R³ is H, fluoro, chloro, C₁₋₆-alkyl, C₁₋₆-haloalkyl, C₁₋₆-alkoxy, C₁₋₆-haloalkoxy or NRᵃRᵇ;
R⁴ is chloro, C₁₋₆-haloalkyl or aryl optionally substituted by halogen; and
Rᵃ and Rᵇ are independently selected from the group consisting of H, C₁₋₆-alkyl and C₂₋₆-hydroxyalkyl;
or a pharmaceutically acceptable salt thereof.

2. The compound of claim 1 wherein:
R¹ is H and R² is —S(O)₂—NRᵃRᵇ or R² is H and R¹ is —S(O)₂—NRᵃRᵇ;
R³ is H, C₁₋₆-alkyl, C₁₋₆-alkoxy, or NRᵃRᵇ;
R⁴ is C₁₋₆-haloalkyl or aryl optionally substituted by halogen;
and Rᵃ and Rᵇ are independently selected from the group consisting of H and C₁₋₆-alkyl;
or a pharmaceutically acceptable salt thereof.

3. The compound of claim 1 wherein R¹ is H and R² is —S(O)₂—NRᵃRᵇ.

4. The compound of claim 3 wherein Rᵃ and Rᵇ are H.

5. The compound of claim 4 selected from the group consisting of:
3'-(8-Methyl-4-oxo-7-trifluoromethyl-4,5-dihydro-3H-benzo[b][1,4]diazepin-2-yl)-biphenyl-4-sulfonic acid amide;
3'-(4-Oxo-7-trifluoromethyl-4,5-dihydro-3H-benzo[b][1,4]diazepin-2-yl)-biphenyl-4-sulfonic acid amide;
3'-(8-Ethoxy-4-oxo-7-trifluoromethyl-4,5-dihydro-3H-benzo[b][1,4]diazepin-2-yl)-biphenyl-4-sulfonic acid amide;

3'-(8-Dimethylamino-4-oxo-7-trifluoromethyl-4,5-dihydro-3H-benzo[b][1,4]diazepin-2-yl)-biphenyl-4-sulfonic acid amide;

3'-[8-(Isobutyl-methyl-amino)-4-oxo-7-trifluoromethyl-4,5-dihydro-3H-benzo[b][1,4]diazepin-2-yl]-biphenyl-4-sulfonic acid amide;

3'-[7-(2-Fluoro-phenyl)-4-oxo-4,5-dihydro-3H-benzo[b][1,4]diazepin-2-yl]-biphenyl-3-sulfonic acid amide; and 3'-(8-Isobutylamino-4-oxo-7-trifluoromethyl-4,5-dihydro-3H-benzo[b][1,4]diazepin-2-yl)-biphenyl-4-sulfonic acid amide.

6. The compound of claim 3 wherein $R^a$ is H and $R^b$ is $C_{1-6}$-alkyl.

7. The compound of claim 6 selected from the group consisting of:
3'-(4-Oxo-7-trifluoromethyl-4,5-dihydro-3H-benzo[b][1,4]diazepin-2-yl)-biphenyl-4-sulfonic acid tert-butylamide; and 3'-(8-Ethoxy-4-oxo-7-trifluoromethyl-4,5-dihydro-3H-benzo[b][1,4]diazepin-2-yl)-biphenyl-4-sulfonic acid tert-butylamide.

8. The compound of formula (I) claim 1 wherein $R^2$ is H and $R^1$ is —S(O)$_2$—NR$^a$R$^b$.

9. The compound of claim 8 wherein $R^a$ and $R^b$ are H.

10. The compound of claim 9 selected from the group consisting of:
3'-(8-Methyl-4-oxo-7-trifluoromethyl-4,5-dihydro-3H-benzo[b][1,4]diazepin-2-yl)-biphenyl-3-sulfonic acid amide;

3'-(4-Oxo-7-trifluoromethyl-4,5-dihydro-3H-benzo[b][1,4]diazepin-2-yl)-biphenyl-3-sulfonic acid amide;

3'-(8-Ethoxy-4-oxo-7-trifluoromethyl-4,5-dihydro-3H-benzo[b][1,4]diazepin-2-yl)-biphenyl-3-sulfonic acid amide;

3'-(8-Dimethylamino-4-oxo-7-trifluoromethyl-4,5-dihydro-3H-benzo[b][1,4]diazepin-2-yl)-biphenyl-3-sulfonic acid amide;

3'-[8-(Isobutyl-methyl-amino)-4-oxo-7-trifluoromethyl-4,5-dihydro-3H-benzo[b][1,4]diazepin-2-yl]-biphenyl-3-sulfonic acid amide;

3'-[7-(2-Fluoro-phenyl)-4-oxo-4,5-dihydro-3H-benzo[b][1,4]diazepin-2-yl]-biphenyl-4-sulfonic acid amide; and 3'-(8-Isobutylamino-4-oxo-7-trifluoromethyl-4,5-dihydro-3H-benzo[b][1,4]diazepin-2-yl)-biphenyl-3-sulfonic acid amide.

11. The compound of claim 8 wherein $R^a$ is H and $R^b$ is $C_{1-6}$-alkyl.

12. The compound of claim 11 selected from the group consisting of:
3'-(8-Methyl-4-oxo-7-trifluoromethyl-4,5-dihydro-3H-benzo[b][1,4]diazepin-2-yl)-biphenyl-3-sulfonic acid tert-butylamide;

3'-(4-Oxo-7-trifluoromethyl-4,5-dihydro-3H-benzo[b][1,4]diazepin-2-yl)-biphenyl-3-sulfonic acid tert-butylamide; and 3'-(8-Ethoxy-4-oxo-7-trifluoromethyl-4,5-dihydro-3H-benzo[b][1,4]diazepin-2-yl)-biphenyl-3-sulfonic acid tert-butylamide.

13. A pharmaceutical composition comprising administering a therapeutically effective amount of a compound of formula I (I)

wherein:
$R^1$ is H and $R^2$ is —S(O)$_2$—NR$^a$R$^b$ or $R^2$ is H and $R^1$ is —S(O)$_2$—NR$^a$R$^b$;

$R^3$ is H, fluoro, chloro, $C_{1-6}$-alkyl, $C_{1-6}$-haloalkyl, $C_{1-6}$-alkoxy, $C_{1-6}$-haloalkoxy or NR$^a$R$^b$;

$R^4$ is chloro, $C_{1-6}$-haloalkyl or aryl optionally substituted by halogen; and $R^a$ and $R^b$ are independently selected from the group consisting of H, $C_{1-6}$-alkyl and $C_{2-6}$-hydroxyalkyl;

or a pharmaceutically acceptable salt thereof and a pharmaceutically acceptable carrier.

* * * * *